United States Patent [19]

Harrison

[11] Patent Number: 5,407,241
[45] Date of Patent: Apr. 18, 1995

[54] CONTACT LENS APPLICATOR

[76] Inventor: Kenneth Harrison, 813 Sussex Rd., Franklyn Lakes, N.J. 07417

[21] Appl. No.: 279,253

[22] Filed: Jul. 21, 1994

[51] Int. Cl.⁶ ............................................. A61F 9/00
[52] U.S. Cl. ..................................... 294/1.2; 206/5.1
[58] Field of Search .......................... 294/1.2; 15/214; 134/901; 206/5.1; 606/107

[56] References Cited

U.S. PATENT DOCUMENTS

| | | | |
|---|---|---|---|
| 2,919,696 | 1/1960 | Rinaldy | 294/1.2 |
| 3,091,328 | 5/1963 | Leonardos | 294/1.2 X |
| 3,343,657 | 9/1967 | Speshyock | 134/901 X |
| 3,344,461 | 10/1967 | Floor | 294/1.2 X |
| 3,645,284 | 2/1972 | Krezanoski et al. | 134/901 X |
| 3,990,579 | 11/1976 | Manning | 134/901 X |
| 4,026,591 | 5/1977 | Cleaveland | 294/1.2 |
| 4,113,297 | 9/1978 | Quinn | 294/1.2 |
| 4,392,569 | 7/1983 | Shoup | 206/5.1 |
| 4,565,396 | 1/1986 | Larimer | 294/1.2 |
| 5,114,686 | 5/1992 | Gillespie | 206/5.1 X |
| 5,246,259 | 9/1993 | Hellenkamp et al. | 294/1.2 |

Primary Examiner—Johnny D. Cherry
Attorney, Agent, or Firm—Brumbaugh, Graves, Donohue & Raymond

[57] ABSTRACT

Apparatus is provided for retaining and applying a contact lens, particularly a disposable, extended-wear lens that tends to be difficult to handle and apply. The apparatus includes a base with a concave cavity that receives an applicator wand with an upper lens receptacle. A retaining member holds the lens and wand in place until the user desires to apply it. Application of the lens can be effected without touching the lens.

4 Claims, 2 Drawing Sheets

CONTACT LENS APPLICATOR

BACKGROUND OF THE INVENTION

The present invention relates to devices for applying contact lenses, and particularly to applying "disposable" contact lenses which are designed for single use and extended wear. Such disposable lenses are supplied in a plastic pouch filled with fluid. When the package is opened, the user must locate the lens in the fluid and manipulate the lens between the fingers to get the lens in condition for application. Since the lens is very thin and flexible, it will frequently fold upon itself or switch to an "inverted" position that is improper for application.

It is an object of the invention to provide an apparatus that provides a convenient packaging for a disposable lens as well as an apparatus for holding the lens while it is applied, such that the lens can be removed from a fluid filled pouch while in the apparatus, drained of excess fluid and applied to the user's eye without manual manipulation or hand contact.

SUMMARY OF THE INVENTION

In accordance with the present invention there is provided an apparatus for retaining and applying a contact lens, comprising a base member having a concave upper chamber having a diameter larger than the lens and an applicator wand having a shaft removably extending through a central bore in the base and having an upper receptacle which comprises radially extending fingers. The periphery of the fingers is smaller than the diameter of the lens and the receptacle and fingers are receivable in the concave chamber. There is finally provided a fluid permeable retaining member having a convex lower surface for insertion into the concave upper chamber and for releasably attaching thereto to hold a lens in the concave chamber against the upper receptacle.

In a preferred embodiment the convex lower surface comprises a mesh and the fingers are flexible and formed into the shape of a concave receptacle.

For a better understanding of the present invention, together with other and further embodiments, reference is made to the following description, taken in conjunction with the accompanying drawings and its scope will be pointed out in the appended claims.

DESCRIPTION OF THE PREFERRED EMBODIMENT

Figure 1:
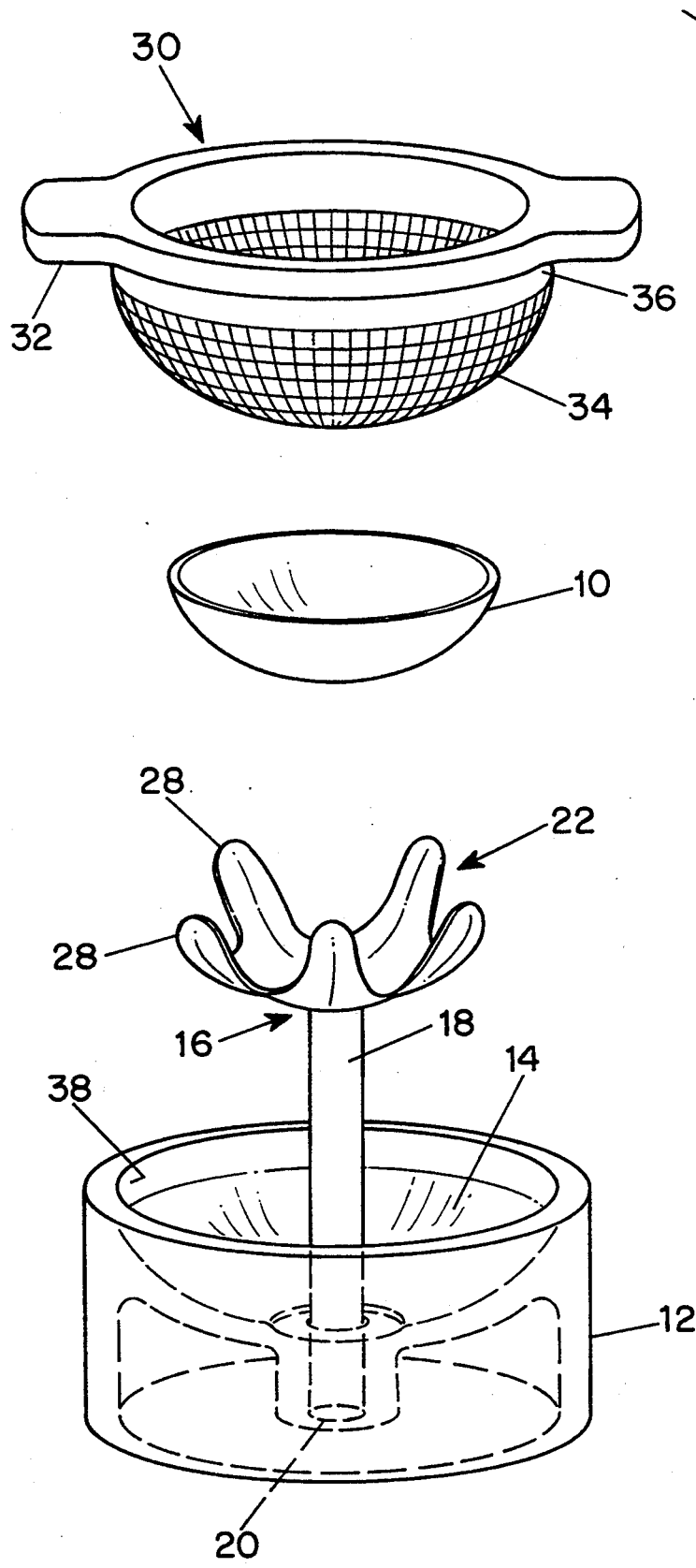
FIG. 1 is a perspective view of the apparatus of the present invention with the parts separated.
Figure 2:
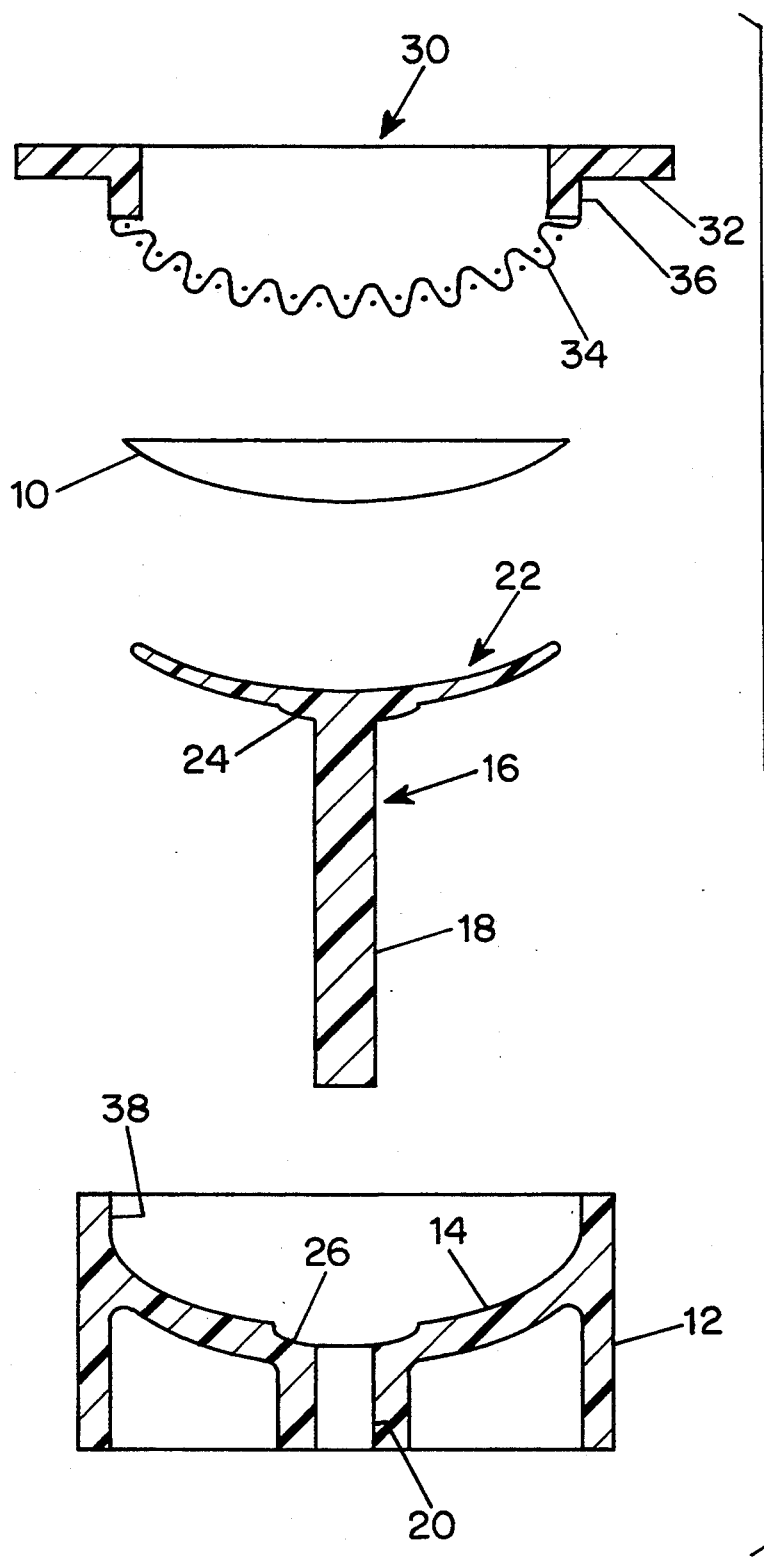
FIG. 2 is a cross sectional view of the FIG. 1 apparatus.

The perspective view of FIG. 1 and cross-section of FIG. 2 show the three parts of the apparatus of my invention with a contact lens 10 in position to be retained and held by the apparatus. The apparatus includes a base member 12, which is cylindrical in shape and includes an upper concave chamber 14. An applicator wand 16 is receivable in base member 12 by having its shaft 18 pass through a central bore 20 in base 12 and having an upper receptacle 22 of applicator wand 16 received in concave chamber 14.

The diameter of concave chamber 14 is selected to be larger than the diameter of a contact lens 10 to be received therein. The receptacle 22 is smaller in diameter than the lens 10, such that when placed on the receptacle 22, the edges of lens 10 extend beyond the periphery of receptacle 22. Preferably, the base of concave chamber 14 is contoured to receive receptacle 22 and other structure of wand 16, such as receptacle base 24, which is receivable in recess 26. Receptacle 22 preferably comprises flexible fingers 28 arranged as petals of a flower, and there may also be provided recesses in concave chamber 14 corresponding to fingers 28.

Retaining member 30 has an upper flange 32 with integrally formed tabs and a lower convex mesh surface 34 arranged for insertion into concave chamber 14 of base 12. A cylindrical portion 36 is arranged to fit closely into cylindrical portion 38 of concave chamber 14 and be retained therein.

When assembled, shaft 18 of wand 16 is pulled all the way into base 12 until receptacle 22 sits on the base of concave chamber 14. Lens 10 is placed in position on receptacle 22 and retaining member 30 is placed over the lens and pressed into the concave chamber such that cylindrical surfaces 36, 38 hold retaining member 30 in position and the convex mesh surface 34 of retaining member 30 holds the lens in position. The entire assembly can then be packaged in fluid.

When the user desires to apply the lens, he can first remove the assembly from the fluid package and drain the fluid from the lens through mesh 34. To aid in the drainage of fluid, base 12 and receptacle 22 may also be provided with drainage openings. By shaking the assembly, the lens can be sufficiently dehydrated for application. The retaining member is then removed using flange 32 while holding base 12. After the retaining member is removed, shaft 18 can be pushed upward and the lens can be presented to the eye with the wand in the position shown in FIG. 1. The user can conveniently grasp base 12 to hold the apparatus. Alternatively, wand 16 can be pushed upward until its upper portion can be grasped by the fingers and then removed from base 12 for presenting the lens in receptacle 22 for insertion into the eye. Thus, the lens can be inserted completely without touching and is presented without possibility of inadvertent inversion. Since the lens 10 is larger than receptacle 22, the receptacle does not touch the eye. Accordingly, possibility of lens contamination is largely avoided, and the difficulty of finding a tiny lens and manipulating the same is eliminated.

While there has been described the preferred embodiment of the invention, those skilled in the art will recognize that other and further changes may be made thereto without departing from the spirit of the invention and it is intended to claim all such changes as fall within he true scope of the invention.

I claim:

1. Apparatus for retaining and applying a contact lens, comprising:
    a base member having a concave upper chamber, said chamber being larger in diameter than said lens;
    an applicator wand having a shaft removeably extending through a central bore in said base member and having an upper receptacle comprising radially extending fingers, the periphery of said fingers being smaller than said lens diameter, said receptacle being receivable in said concave chamber; and
    a fluid permeable retaining member having a convex lower surface for insertion into said concave upper chamber and being arranged to releasably connect to said base member to hold a lens in said concave chamber against said upper receptacle.

2. Apparatus as specified in claim 1 wherein said convex lower surface of said retaining member comprises a mesh.

3. Apparatus as specified in claim 1 wherein said fingers are flexible.

4. Apparatus as specified in claim 1 wherein said fingers are shaped into a concave receptacle.

* * * * *